United States Patent
Cole et al.

(10) Patent No.: US 6,770,642 B2
(45) Date of Patent: Aug. 3, 2004

(54) INDOLYLALKYLAMINE DERIVATIVES AS 5-HYDROXYTRYPTAMINE-6 LIGANDS

(75) Inventors: Derek Cecil Cole, New City, NY (US); Joseph Raymond Stock, Monroe, NY (US); William Joseph Lennox, South Plainfield, NJ (US); Ping Zhou, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/323,369

(22) Filed: Dec. 19, 2002

(65) Prior Publication Data

US 2003/0171353 A1 Sep. 11, 2003

Related U.S. Application Data

(60) Provisional application No. 60/342,907, filed on Dec. 20, 2001.

(51) Int. Cl.⁷ .................... C07D 513/04; C07D 209/08; C07D 471/04; A61K 31/4162; A61P 25/18
(52) U.S. Cl. .................... 514/233.2; 548/154; 548/151; 514/368; 514/300; 514/360; 514/254.02; 546/121; 544/318; 544/133
(58) Field of Search ................................. 548/154, 151; 514/368, 300, 366, 254.02, 233.2; 546/121; 544/318, 133

(56) References Cited

U.S. PATENT DOCUMENTS

| | | |
|---|---|---|
| 5,545,644 A | 8/1996 | Macor et al. |
| 6,133,287 A | 10/2000 | Slassi et al. |
| 6,187,805 B1 | 2/2001 | Pineiro et al. |
| 6,194,410 B1 | 2/2001 | Bös et al. |
| 6,403,808 B1 | 6/2002 | Glennon et al. |

FOREIGN PATENT DOCUMENTS

| | | |
|---|---|---|
| WO | WO 01/12629 A1 | 2/2001 |
| WO | WO 01/32660 A1 | 5/2001 |

OTHER PUBLICATIONS

Branchek and Blackburn, 5–HT6 receptors as emerging targets for drug discovery, Annu. Rev. Pharmcol. Toxicol. 40:319–334, 2000.*

Y. Tsai et al, $N_1$–(Benzenesulfonyl)tryptamines as Novel $5OHT_6$ Antagonists, Bioorganic & Medicinal Chemistry Letters 10 (2000) 2295–2299.

M. G. N. Russell et al, N–Arylsulfonylindole Derivatives as Serotonin 5OHT6 Receptor Ligands, Journal of Medicinal Chemistry 44 (2001) 3881–3895.

R. A. Glennon et al, 2–Substituted Tryptamines: Agents with Selectivity for 5–$HT_6$ Serotonin Receptors, Journal of Medicinal Chemistry 43 (2000) 1011–1018.

* cited by examiner

*Primary Examiner*—Richard L. Raymond
*Assistant Examiner*—Hong Liu
(74) *Attorney, Agent, or Firm*—Barbara L. Lences

(57) ABSTRACT

The present invention provides a compound of formula I and the use thereof for the therapeutic treatment of disorders relating to or affected by the 5-HT6 receptor.

(I)

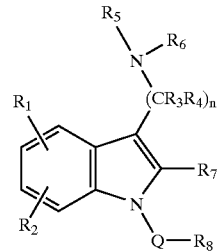

19 Claims, No Drawings

INDOLYLALKYLAMINE DERIVATIVES AS 5-HYDROXYTRYPTAMINE-6 LIGANDS

This application claims priority from copending provisional application serial No. 60/342,907, filed on Dec. 20, 2001, the entire disclosure of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides an indolylalkylamine derivative of formula I

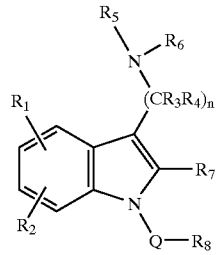

wherein

Q is $SO_2$, CO, $CONR_9$ or $CSNR_{10}$;

n is an integer of 2 or 3;

$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$ and $R_4$ are each independently H or an optionally substituted $C_1$–$C_6$alkyl group;

$R_5$ and $R_6$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;

$R_7$ is H, halogen, or a $C_1$–$C_6$alkyl, $C_1$–$C_6$alkoxy, aryl or heteroaryl group each optionally substituted;

$R_8$ is an optionally substituted 8- to 13-membered bicyclic or tricyclic ring system having a N atom at the bridgehead and optionally containing 1, 2 or 3 additional heteroatoms selected from N, O or S;

m is 0 or an integer of 1 or 2;

$R_9$ and $R_{10}$ are each independently H or a $C_1$–$C_6$alkyl, aryl or heteroaryl group each optionally substituted;

$R_{12}$, $R_{13}$, $R_{19}$ and $R_{23}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$, $R_{15}$ and $R_{22}$ are each independently H or an optionally substituted $C_1$–$C_6$alkyl group; and $R_{16}$, $R_{17}$, $R_{18}$, $R_{20}$ and $R_{21}$ are each independently H or an optionally substituted $C_1$–$C_4$alkyl group; or $R_{20}$ and $R_{21}$ may be taken together with the atom to which they are attached to form a 5- to 7-membered ring optionally containing another heteroatom selected from O, N or S; or the stereoisomers thereof or the pharmaceutically acceptable salts thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that indolylalkylamine derivatives of formula I demonstrate 5-HT6 affinity. Advantageously, said amine derivatives may be used as effective therapeutic agents for the treatment of central nervous system (CNS) disorders associated with or affected by the 5-HT6 receptor. Accordingly, the present invention provides indolylalkylamine derivatives of formula I

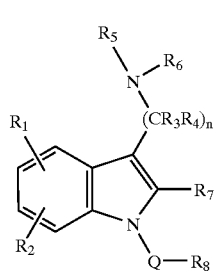

(I)

wherein

Q is $SO_2$, CO, $CONR_9$ or $CSNR_{10}$;

n is an integer of 2 or 3;

$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$ and $R_4$ are each independently H or an optionally substituted $C_1$–$C_6$alkyl group;

$R_5$ and $R_6$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;

$R_7$ is H, halogen, or a $C_1$–$C_6$alkyl, $C_1$–$C_6$alkoxy, aryl or heteroaryl group each optionally substituted;

$R_8$ is an optionally substituted 8- to 13-membered bicyclic or tricyclic ring system having a N atom at the bridgehead and optionally containing 1, 2 or 3 additional heteroatoms selected from N, O or S;

m is 0 or an integer of 1 or 2;

$R_9$ and $R_{10}$ are each independently H or a $C_1$–$C_6$alkyl, aryl or heteroaryl group each optionally substituted;

$R_{12}$, $R_{13}$, $R_{19}$ and $R_{23}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$, $R_{15}$ and $R_{22}$ are each independently H or an optionally substituted $C_1$–$C_6$alkyl group; and $R_{16}$, $R_{17}$, $R_{18}$, $R_{20}$ and $R_{21}$ are each independently H or an optionally substituted $C_1$–$C_4$alkyl group; or $R_{20}$ and $R_{21}$ may be taken together with the atom to which they are attached to form a 5- to 7-membered ring optionally containing another heteroatom selected from O, N or S; or the stereoisomers thereof or the pharmaceutically acceptable salts thereof.

As used in the specification and claims, the term halogen designates Br, Cl, I or F and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein W is NR, O or S; and R is H or an optional substituent as described hereinbelow:

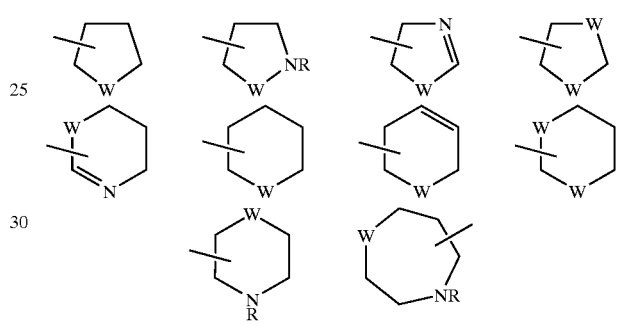

Similarly, as used in the specification and claims, the term heteroaryl designates a 5- to 10-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system, e.g. of 6 to 10 carbon atoms such as phenyl, naphthyl, or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at a bridgehead and optionally containing 1, 2 or 3 additional heteroatoms selected from N, O or S included in the term as designated herein are the following ring systems wherein W is NR, O or S; and R is H or an optional substituent as described hereinbelow:

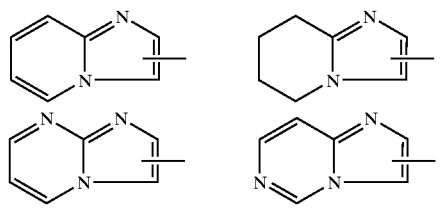

-continued

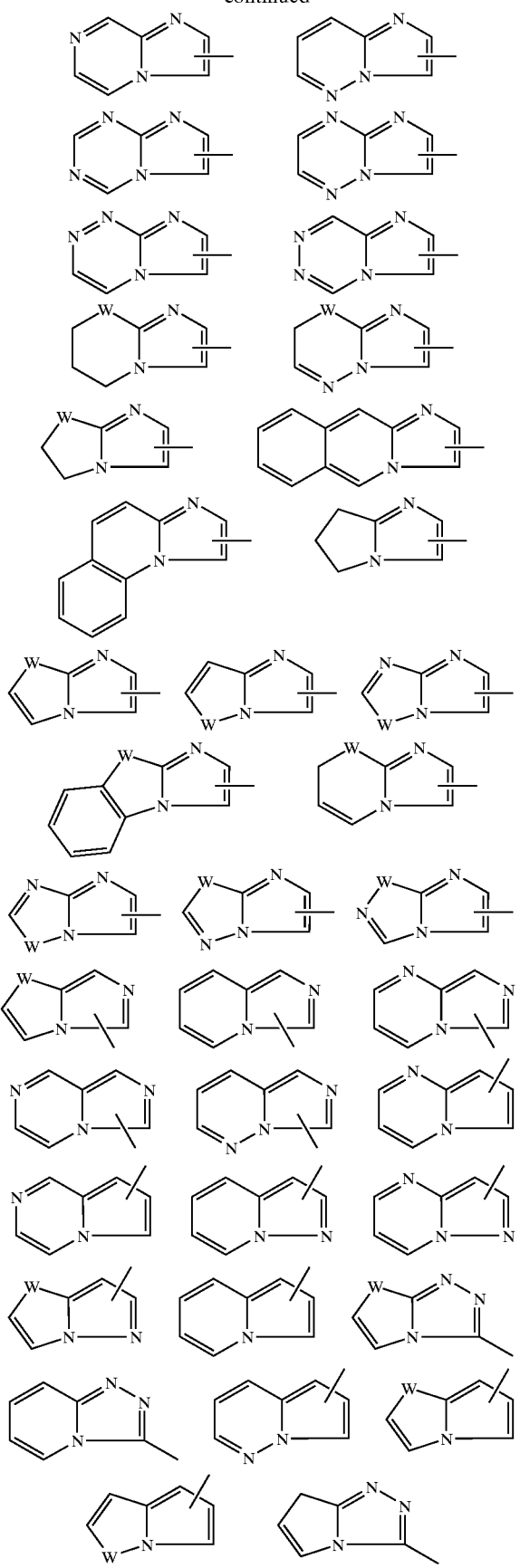

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl, heteroaryl or 8- to 13-membered bicyclic or tricyclic ring system having a N atom at the bridgehead are designated as being optionally substituted, the substituent groups which are optionally present may be one or more, e.g. two or three, the same or different of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heteroaryl, cycloheteroalkyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein Q is $SO_2$. Also preferred are those compounds of formula I wherein n is 2. Another group of preferred compounds of formula I are those compounds wherein $R_8$ is 6-chloroimidazo[2,1-b][1,3]-thiazol-5-yl.

More preferred compounds of the invention are those compounds of formula I wherein Q is $SO_2$ and $R_7$ is H. Another group of more preferred compounds are those compounds of formula I wherein Q is $SO_2$, n is 2 and $R_7$ is H. Further more preferred compounds are those formula I compounds wherein Q is $SO_2$, n is 2, $R_7$ is H and $R_8$ is 6-chloroimidazo[2,1-b][1,3]thiazol-5-yl.

Among the preferred compounds of the invention are:

2-{1-[(6-chloroimidazo[2,1-b][1,3]thiazol-5-yl)sulfonyl]-1H-indol-3-yl}ethylamine;
2-{1-[(imidazo[2,1-b][1,3]thiazol-5-yl)sulfonyl]-1H-indol-3-yl}ethylamine;
{2-[1-(6-chloro-imidazo[2,1-b][1,3]thiazole-5-sulfonyl)-1H-indol-3-yl]ethyl}methylamine;
{2-[1-(6-chloro-imidazo[2,1-b][1,3]thiazole-5-sulfonyl)-1H-indol-3-yl]ethyl}dimethylamine;
benzyl-{2-[1-(6-chloro-imidazo[2,1-b][1,3]thiazole-5-sulfonyl)-1H-indol-3-yl]ethyl}amine;
1-(6-chloro-imidazo[2,1-b][1,3]thiazole-5-sulfonyl)-3-(2-pyrrolidin-1-ylethyl)-1H-indole;
1-(6-chloro-imidazo[2,1-b][1,3]thiazole-5-sulfonyl)-3-[2-(4-methylpiperazin-1-yl)ethyl]-1H-indole;
1-(6-chloro-imidazo[2,1-b][1,3]thiazole-5-sulfonyl)-3-(2-piperidin-1-ylethyl)-1H-indole;
benzyl-{2-[1-(6-chloro-imidazo[2,1-b][1,3]thiazole-5-sulfonyl)-1H-indol-3-yl]ethyl}methylamine;
{2-[1-(6-chloro-imidazo[2,1-b][1,3]thiazole-5-sulfonyl)-1H-indol-3-yl]ethyl}phenethylamine;
1-{2-[1-(6-chloro-imidazo[2,1-b][1,3]thiazole-5-sulfonyl)-1H-indol-3-yl]ethyl}pyrrolidine-2-carboxylic acid;
2-[1-(6-chloro-imidazo[2,1-b][1,3]thiazole-5-sulfonyl)-1H-indol-3-yl]-1-methylethylamine;
(R)-2-[1-(6-chloro-imidazo[2,1-b][1,3]thiazole-5-sulfonyl)-1H-indol-3-yl]-1-methylethylamine;
(S)-2-[1-(6-chloro-imidazo[2,1-b][1,3]thiazole-5-sulfonyl)-1H-indol-3-yl]-1-methylethylamine;
2-[1-(2-chloro-imidazo[1,2-a]pyridine-3-sulfonyl)-1H-indol-3-yl]ethylamine;
2-[1-(2,6-dichloro-imidazo[2,1-b][1,3]thiazole-5-sulfonyl)-1H-indol-3-yl]ethylamine;
2-[1-(2-chloro-benzo[d]imidazo[2,1-b][1,3]thiazole-3-sulfonyl)-1H-indol-3-yl]ethylamine;
{2-[1-(2-chloro-imidazo[1,2-a]pyridine-3-sulfonyl)-1H-indol-3-yl]ethyl}methylamine;
{2-[1-(2,6-dichloro-imidazo[2,1-b][1,3]thiazole-5-sulfonyl)-1H-indol-3-yl]ethyl}methylamine;
{2-[1-(2-chloro-benzo[d]imidazo[2,1-b][1,3]thiazole-3-sulfonyl)-1H-indol-3-yl]ethyl}methylamine;
{2-[1-(2-chloro-imidazo[1,2-a]pyridine-3-sulfonyl)-1H-indol-3-yl]ethyl}dimethyamine;
{2-[1-(2,6-dichloro-imidazo[2,1-b][1,3]thiazole-5-sulfonyl)-1H-indol-3-yl]ethyl}dimethylamine;
{2-[1-(2-chloro-benzo[d]imidazo[2,1-b][1,3]thiazole-3-sulfonyl)-1H-indol-3-yl]ethyl}dimethylamine;
2-[5-chloro-1-(6-chloro-imidazo[2,1-b][1,3]thiazole-5-sulfonyl)-1H-indol-3-yl]ethylamine;
2-[5-chloro-1-(2-chloro-imidazo[1,2-a]pyridine-3-sulfonyl)-1H-indol-3-yl]ethylamine;
2-[5-chloro-1-(2,6-dichloro-imidazo[2,1-b][1,3]thiazole-5-sulfonyl)-1H-indol-3-yl]ethylamine;
2-[5-chloro-1-(2-chloro-benzo[d]imidazo[2,1-b][1,3]thiazole-3-sulfonyl)-1H-indol-3-yl]-ethylamine;
2-[1-(6-chloro-imidazo[2,1-b][1,3]thiazole-5-sulfonyl)-5-methoxy-1H-indol-3-yl]ethylamine;
2-[1-(6-chloro-imidazo[2,1-b][1,3]thiazole-5-sulfonyl)-6-methoxy-1H-indol-3-yl]ethylamine;
2-[5-bromo-1-(6-chloro-imidazo[2,1-b][1,3]thiazole-5-sulfonyl)-1H-indol-3-yl]ethylamine;
2-[5-benzyloxy-1-(6-chloro-imidazo[2,1-b][1,3]thiazole-5-sulfonyl)-1H-indol-3-yl]ethylamine;
2-[1-(6-chloro-imidazo[2,1-b][1,3]thiazole-5-sulfonyl)-5-methyl-1H-indol-3-yl]ethylamine;
2-[1-(6-chloro-imidazo[2,1-b][1,3]thiazole-5-sulfonyl)-6-methyl-1H-indol-3-yl]ethylamine;
2-[1-(6-chloro-imidazo[2,1-b][1,3]thiazole-5-sulfonyl)-7-methyl-1H-indol-3-yl]ethylamine;
3-(2-amino-ethyl)-1-(6-chloro-imidazo[2,1-b][1,3]thiazole-5-sulfonyl)-1H-indol-5-ol;
2-[1-(6-chloro-imidazo[2,1-b][1,3]thiazole-5-sulfonyl)-5-fluoro-1H-indol-3-yl]ethylamine;
2-[1-(6-chloro-imidazo[2,1-b][1,3]thiazole-5-sulfonyl)-6-fluoro-1H-indol-3-yl]ethylamine;

the stereoisomers thereof; or the pharmaceutically acceptable salts thereof.

Compounds of the invention may be conveniently prepared using conventional synthetic methods and, if required, standard separation and isolation techniques. For example, compounds of formula I wherein Q is $SO_2$, n is 2 and $R_3$ and $R_4$ are H (Ia) may be prepared by sequentially reacting an indole derivative of formula I with oxalyl chloride and an amine, $HNR_5R_6$, to give the intermediate of formula III; reducing the carbonyl groups of formula III with lithium aluminum hydride to give the corresponding 3-ethylamine derivative of formula IV; and reacting said formula IV derivative with a base such as potassium t-butoxide or sodium hydride followed by a sulfonyl chloride, $R_8SO_2Cl$, to give the desired formula Ia product. The reaction sequence is shown in flow diagram I.

Flow Diagram I

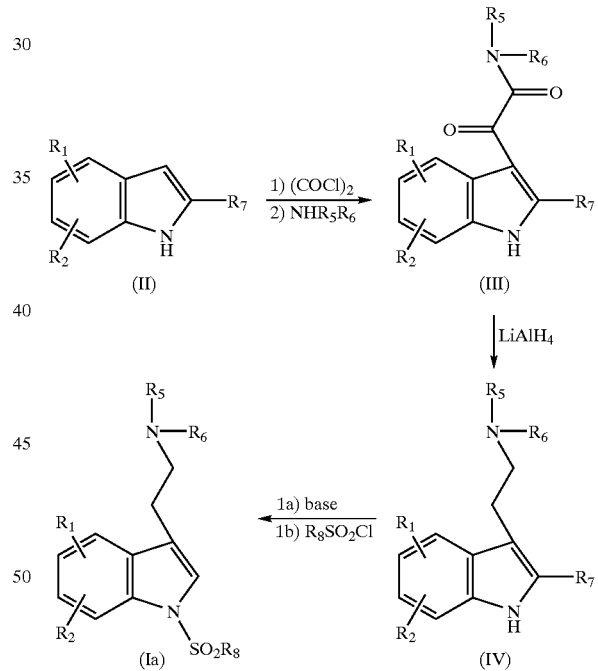

For intermediates of formula IV wherein $R_5$ or $R_6$ are H, the formula IV amine may be protected with a conventional protecting reagent such as di-t-butyl carbonate, prior to the final sulfonylation steps. The resulting N-protected formula I compound may then be deprotected in the presence of acid.

Alternatively, compounds of formula Ia may be prepared by reacting a 3-(2-bromoethyl) derivative of formula V sequentially with a base and a sulfonyl chloride, $R_8SO_2Cl$, to give the formula VI intermediate and reacting the formula VI intermediate with an amine, $HNR_5R_6$ to give the desired product of formula Ia. The reaction steps are shown in flow diagram II Flow Diagram II

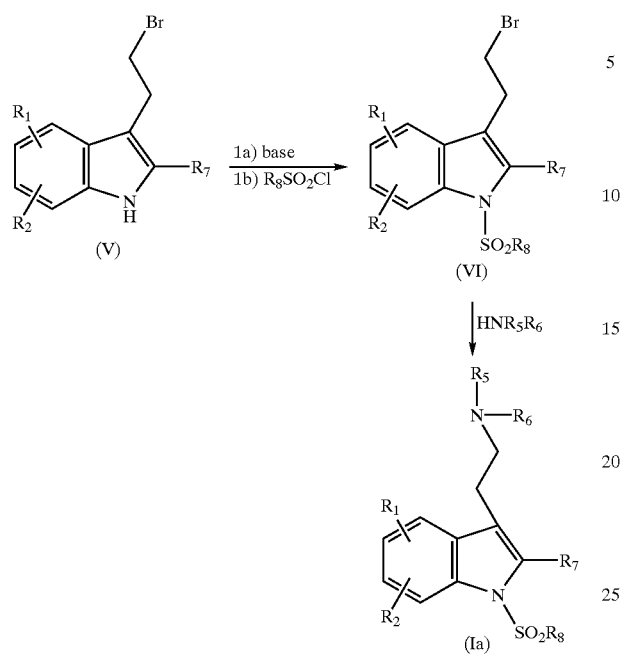

Compounds of formula I wherein $R_3$ or $R_4$ are other than H and Q is $SO_2$ (Ib) may be prepared by sequentially reacting the intermediate of formula II with a Grignard reagent, such as ethyl magnesium bromide, and an amino acid chloride of formula VII to give the 3-acylated compound of formula VIII; reducing said formula VIII compound with a reducing agent such as lithium aluminum hydride to give the corresponding 3-alkylamino compound of formula IX and sulfonating the formula IX compound as described hereinabove in flow diagrams I and II to afford the desired formula Ib product. The reaction sequence is shown in flow diagram III.

Flow Diagram III

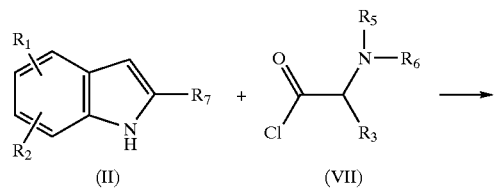

In the case where $R_5$ or $R_6$ are H, the nitrogen atom of the amino acid chloride of formula VII is protected and the corresponding resultant product may be deprotected using conventional means to give the desired formula Ib compound wherein $R_5$ or $R_6$ are H.

Compounds of formula I wherein Q is $SO_2$; n is 3; and $R_3$, $R_4$, $R_5$, $R_6$ and $R_7$ are H (Ic) may be prepared by sequentially reacting an aryl hydrazine hydrochloride of formula X with 3,4-dihydro-2H-pyran to give the indol-3-yl-propanol-1-ol of formula XI; displacing the hydroxy group with bromine to give the corresponding bromo compound of formula XII; reacting the formula XII compound with sodium azide to form the azide of formula XIII; sulfonylating the formula XIII azide to give the compound of formula XIV and converting the formula XIV compound to the desired formula Ic amine via reaction with triphenylphosphine. The reaction sequence is shown in flow diagram IV.

Flow Diagram IV

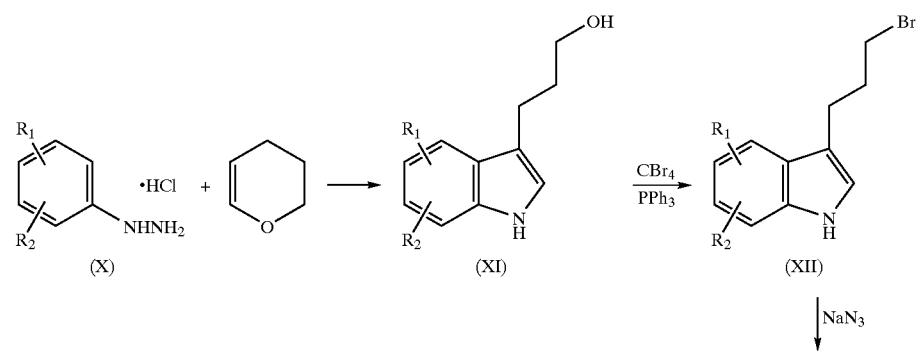

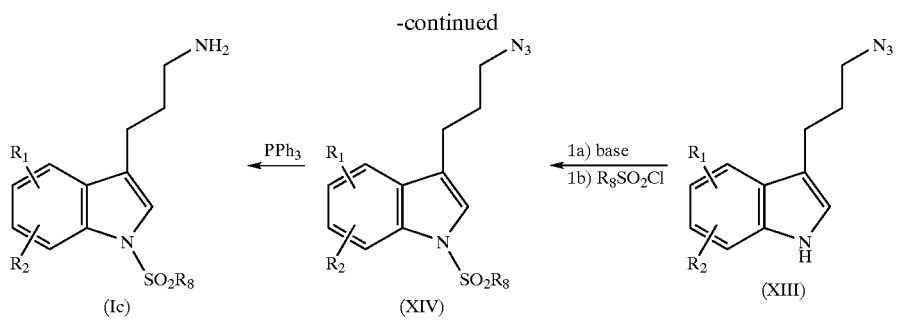

Similarly, compounds of formula I wherein Q is CO, CONR$_9$ or CSNR$_{10}$ may be prepared using the above procedures illustrated in flow diagrams I, II, III and IV and employing the appropriately substituted acid chloride, isocyanate or isothiocyanate in place of R$_8$SO$_2$Cl.

Protecting groups useful in the reactions described hereinabove include t-butylcarboxylate, benzyl, acetyl, benzyloxycarbonyl, or any conventional group known to protect a basic nitrogen in standard synthetic procedures.

Sulfonyl chlorides, R$_8$SO$_2$Cl, may be obtained commercially or prepared by conventional techniques. For example, 6-substituted-imidazo[2,1-b][1,3]thiazol-5-yl sulfonyl chlorides of formulas Xva and Xvb may be prepared by reacting 2-amino thiazole with chloroacetic acid or a suitable chloromethyl ketone to give 2-imino-4-thiazolin-3-ylacetic acid (XVIa) or the 2-imino-4-thiazolin-3-yl ketone (XVIb), respectively; reacting either XVIa or XVIb with POCl$_3$ to give, in the case of XVIa, 6-chloroimidazo[2,1-b]thiazole (XVIIa) or, in the case of XVIb, 6-substituted-imidazo[2,1-b]thiazole XVIIb; and sequentially reacting the respective XVIIa and XVIIb compounds with chlorosulfonic acid and POCl$_3$ to give the desired sulfonyl chlorides of formulas Xva and Xvb. The reactions are illustrated in flow diagram V wherein R represents an optional substituent as described hereinabove with the exclusion of halogen.

Flow Diagram V

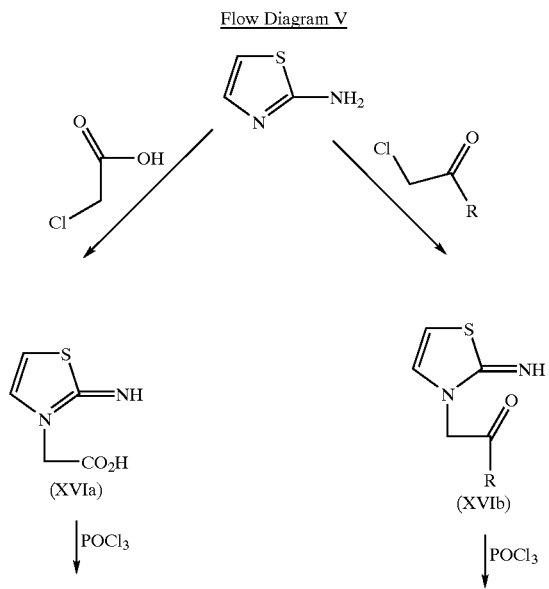

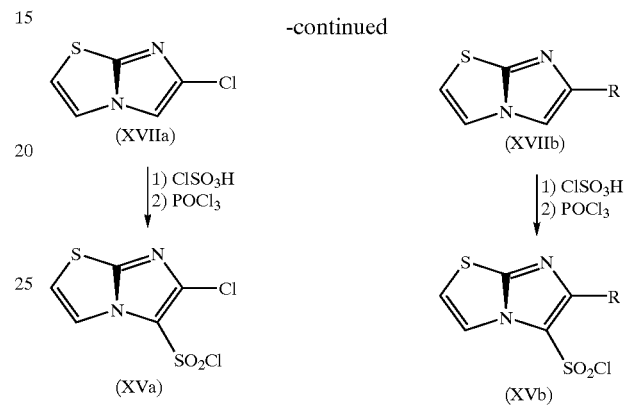

Advantageously, the present invention provides a method for the preparation of a compound of formula I wherein Q is SO$_2$ and R$_5$ and R$_6$ are other than H (Id) which comprises reacting a compound of formula XVIII with a sulfonyl chloride, R$_8$SO$_2$Cl, in the presence of a base optionally in the presence of a solvent. The process is shown in flow diagram VI.

Flow Diagram VI

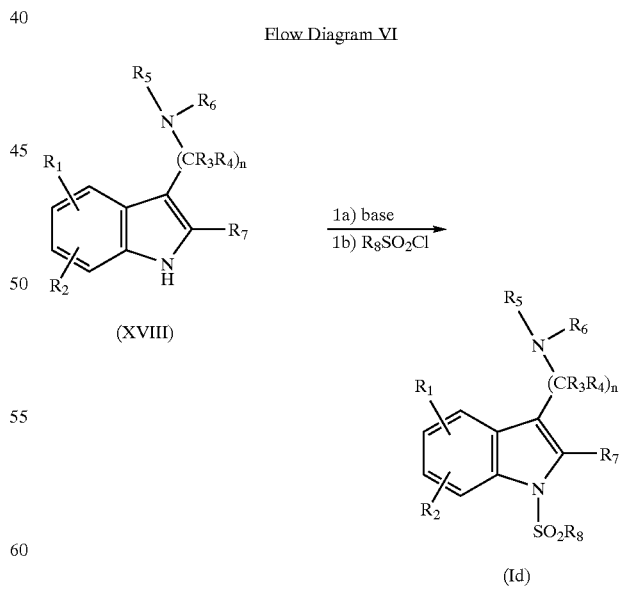

Bases suitable for use in the method of invention are strong bases such as NaH, KOt-Bu, or any conventional base capable of removing a proton from a basic indole or benzazole nitrogen atom.

Advantageously, the inventive compound of formula I may be utilized in the treatment of central nervous system disorders relating to or affected by the 5-HT6 receptor such as motor, mood, psychiatric, cognitive, neurodegenerative, or the like disorders, for example, Alzheimer's disease, Parkinson's disease, attention deficit disorder, anxiety, epilepsy, depression, obsessive compulsive disorder, migraine, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms NMR and HPLC designate nuclear magnetic resonance and high performance liquid chromatography, respectively. The terms THF and EtOAc designate tetrahydrofuran and ethyl acetate, respectively.

EXAMPLE 1

Preparation of 2-{1-[(6-Chloroimidazo[2,1-b][1,3]thiazole-5-yl)sulfonyl]-1H-indol-3-yl}ethylamine Hydrochloride

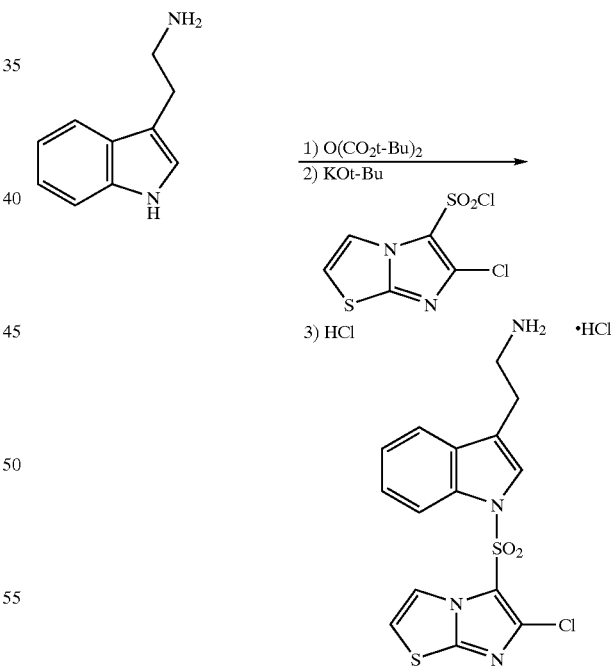

A solution of tryptamine (4.2 g, 26.2 mmol) in a 1:1 mixture of acetone; water is treated with di-t-butyl carbonate (6.5 g, 27.8 mmol) and $K_2CO_3$ (7.5 g, 54.4 mmol), stirred at room temperature for 16 h, concentrated in vacuo to an aqueous mixture and extracted with EtOAc. The extracts are combined, dried over $MgSO_4$ and concentrated in vacuo. A mixture of the resultant residue (5.6 g, 21 mmol) and 6-chloroimidazo[2,1-b]thiazole-5-sulfonyl chloride (5.01 g, 19.5 mmol) in THF is treated portion-wise with potassium t-butoxide (4.3 g, 39 mmol (2 eq.) at room temperature, stirred for 16 h, poured into a saturated NaHCO₃ solution and extracted with EtOAc. The extracts are combined, dried over MgSO₄ and concentrated in vacuo. This resultant residue is chromatographed (silica gel, 10%–60% EtOAc in hexanes as gradient eluent) to give the protected 5-sulfonyl-tryptamine intermediate as a tan solid, 5.6 g (60% yield). A solution of said intermediate (6.8 g 14.2 mmol) in isopropanol is treated with 4N HCl in dioxane (40 mL, 11 equiv.), stirred for 4 h and filtered. The filtercake is washed with ether and air-dried to give the title product as an off-white solid 3.2 g (55% yield) mp 239–241° C., identified by NMR and mass spectral analyses.

EXAMPLE 2

Preparation of 3-(2-bromoethyl)-1-(6-chloroimidazo[2,1-b]thiazole-5-sulfonyl)indole

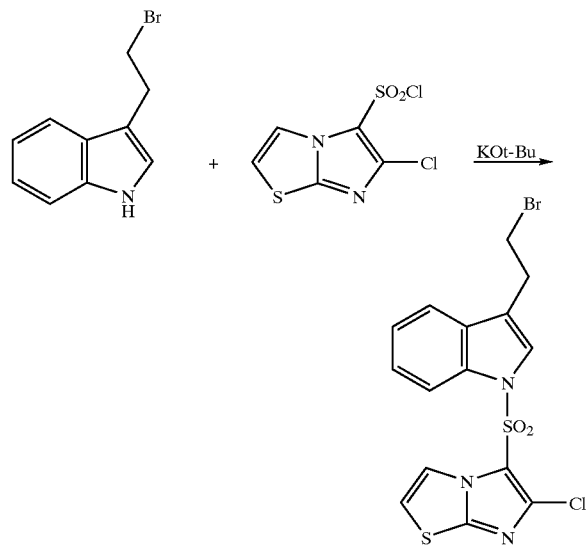

A mixture of 3-(2-bromoethyl)indole (1.0 g, 4.46 mmol) and 6-chloroimidazo[2,1-b]thiazole-5-sulfonyl chloride (0.96 g, 1.1 eq.) in THF is treated with potassium t-butoxide (0.48 g, 1.1 equiv.) at room temperature, stirred for 16 h, quenched with saturated NaHCO₃ and extracted with EtOAc. The extracts are combined, dried over MgSO₄ and concentrated in vacuo to give the title product as a brown oil, 1.2 g (58% yield), identified by HPLC and mass spectral analyses.

EXAMPLE 3

Preparation of {2-[1-(6-Chloroimidazo[2,1-b]thiazole-5-sulfonyl)-1H-indol-3-yl]ethyl}methyl amine

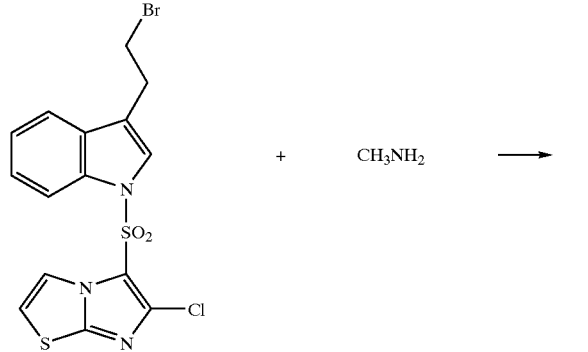

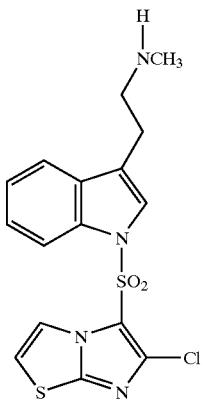

A solution of 3-(2-bromoethyl)-1-(6-chloroimidazo[2,1-b]thiazole-5-sulfonyl)indole (92 mg, 0.20 mmol) in THF is treated with methyl amine (2M in methanol, 0.4 mL, 2 eq.), heated at 50° C. for 24 h, cooled and concentrated in vacuo. The resultant residue is purified by HPLC[1] to give the title product as a white solid, 18.5 mg, identified by HPLC[2] and mass spectral analyses.

[1]HPLC conditions (preparative): Gilson Preparative HPLC system; YMC Pro C18, 20 mm×50 mm ID, 5 uM column; 2 mL injection; Solvent A: 0.02% TFA/water; Solvent B: 0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.
[2]HPLC conditions (analytical): Hewlett Packard 1100 HPLC system; Waters Xterra C18, 2 mm×30 mm ID, 3 uM column; 5 uL injection; Solvent A: 0.02% TFA/water; Solvent B: 0.02% TFA/acetonitrile; Gradient: Time 0: 95% A; 0.2 min: 95% A; 3 min: 5% A; Flow rate 1.2 mL/min; Detection: 254 nm DAD.

EXAMPLE 4–11

Preparation of N-Substituted-2-{1-[(6-Chloroimidazo[2,1-b][1,3]thiazol-5-yl)sulfonyl]-1H-indol-3-yl}ethylamine Derivatives

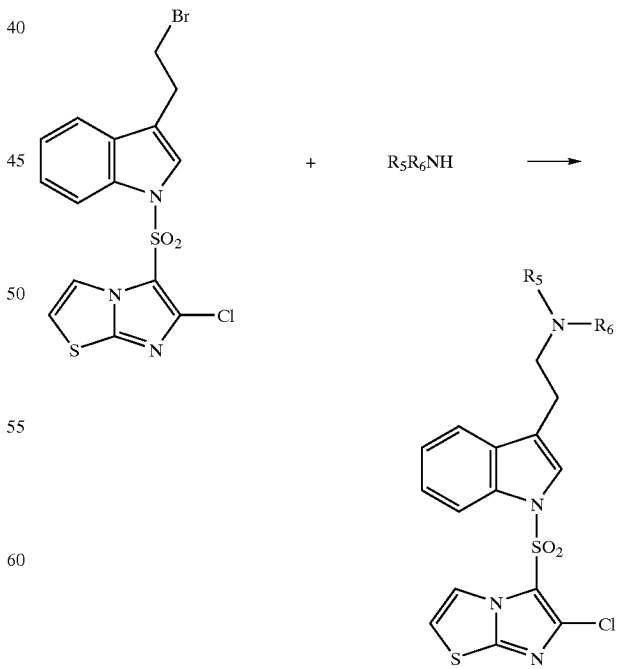

Using essentially the same procedures described hereinabove and employing the appropriate amine, the compounds shown in Table I are obtained and identified by HPLC and mass spectral analyses.

TABLE I

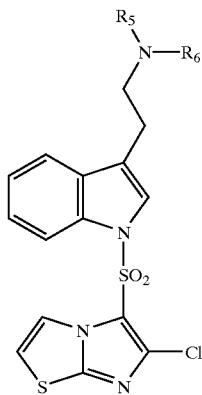

| Ex. No. | R5 | R6 | HPLC[1] min. | M + H |
|---|---|---|---|---|
| 4 | CH$_3$ | CH$_3$ | 1.75 | 410 |
| 5 | H | CH$_2$C$_6$H$_5$ | 2.01 | 472 |
| 6 | —CH$_2$—CH$_2$—CH$_2$—CH$_2$— | | 1.74 | 436 |
| 7 | —CH$_2$—CH$_2$—N(CH$_3$)—CH$_2$—CH$_2$— | | 1.69 | 465 |
| 8 | —CH$_2$—CH$_2$—O—CH$_2$—CH$_2$ | | 1.67 | 450 |
| 9 | CH$_3$ | CH$_2$C$_6$H$_5$ | 1.88 | 486 |
| 10 | H | CH$_2$CH$_2$C$_6$H$_5$ | 1.90 | 486 |
| 11 | —CH(CO$_2$H)—CH$_2$—CH$_2$—CH$_2$— | | 1.96 | 480 |

[1]HPLC conditions (analytical): Hewlett Packard 1100 HPLC system; Waters Xterra C18, 2 mm × 30 mm ID, 3 uM column; 5 uL injection; Solvent A: 0.02% TFA/water; Solvent B: 0.02% TFA/acetonitrile; Gradient: Time 0: 95% A; 0.2 min: 95% A; 3 min: 5% A; Flow rate 1.2 mL/min; Detection: 254 nm DAD.

EXAMPLE 12

Preparation of 2[1-(6-Chloroimidazo[2,1-b]thiazole-5-sulfonyl)-1H-indol-3-yl]-1-methylethylamine Hydrochloride

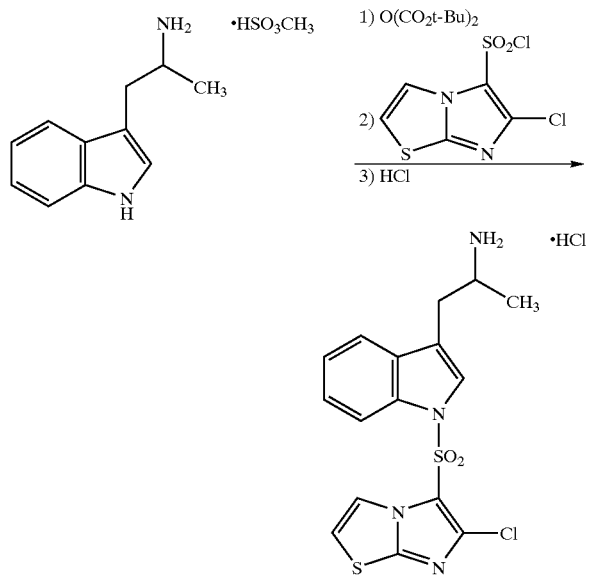

A solution of a-methyltryptamine methane sulfonate (5.0 g, 18.5 mmol) in a 1:1 mixture of acetone:water is treated with di-t-butyl dicarbonate (7.7 g, 55.5 mmol, 3 eq.), stirred at room temperature for 16 h, concentrated to an aqueous mixture and extracted with EtOAc. The extracts are combined, dried over MgSO$_4$ and concentrated in vacuo. A mixture of a portion of the resultant residue (2.0 g, 7.3 mmol, 1.1 eq.) and 6-chloroimidazo[2,1-b]thiazole-5-sulfonyl chloride (1.7 g, 6.6 mmol, 1.0 eq.) in THF is treated portionwise with potassium t-butoxide (820 mg, 7.3 mmol, 1.1 equiv.) at room temperature stirred for 1 h, poured into saturated NaHCO$_3$ and extracted with EtOAc. The extracts are combined, dried over Na$_2$SO$_4$ and concentrated in vacuo. This resultant residue is chromatographed (silica gel, 20%–50% EtOAc in hexanes as gradient eluent) to give the free base of the title product as a brown oil, 1.7 g (50% yield). Treatment with 4N HCl in dioxane and THF, followed by filtration and recrystallization of the filtercake from ethanol affords the title product as a light brown solid 1.0 g (40% yield), identified by NMR and mass spectral analyses.

EXAMPLE 13

Preparation of (S)-2-Amino-1-(1H-indol-3-yl)-propan-1-one

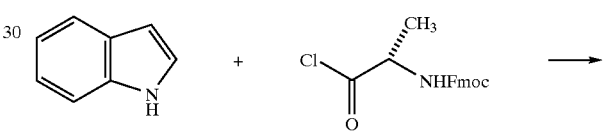

A solution of indole (1.1 g, 9.3 mmol, 1.0 eq.) in methylene chloride under N$_2$ at 0° C. is treated dropwise with ethyl magnesium bromide (9 mL 3.0M in ether, 27 mmol, 3 equiv.), allowed to warm to room temperature for 1H, cooled to 0° C., treated dropwise with a solution of Fmoc-L-alanine acid chloride (14.0 mmol, 1.5 eq.) in methylene chloride, allowed to warm to room temperature for 1 h, poured over 50 mL of aqueous 1N HCl, cooled to 0° C. and stirred at 0° C. for 15 minutes. The phases are separated. The organic phase is dried over Na$_2$SO$_4$ and concentrated in vacuo to give a residue. The residue is diluted with saturated NaHCO$_3$ and extracted with EtOAc. The extracts are combined and concentrated in vacuo to give a residue which is dissolved in 10% piperidine in dimethyl formamide and stirred for 1 h at room temperature. The resultant solution is diluted with saturated NaHCO$_3$ and extracted with EtOAc. The extracts are combined, dried over MgSO$_4$ and concentrated in vacuo to afford the title product as a brown oil, 0.8 g (47% yield), identified by HPLC and mass spectral analyses.

EXAMPLE 14

Preparation of (S)-2-(1H-Indol-3-yl)-1-methylethylamine

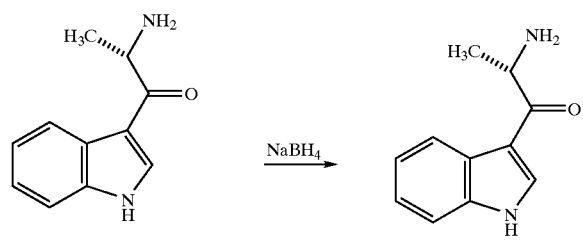

A solution of (S)-2-amino-1-(1H-indol-3-yl)-propan-1-one (0.47 g, 2.5 mmol, 1.0 eq.) in acetonitrile and isopropanol is treated portionwise with NaBH$_4$ (285 mg, 7.49 mmol, 3.0 equiv.), heated at reflux temperature for 24 h, stirred at room temperature under N$_2$ for 36 h, quenched with methanol, concentrated and partitioned between water and EtOAc. The EtOAc phase is dried over MgSO$_4$ and concentrated in vacuo to afford the title product as a brown oil, identified by HPLC and mass spectral analyses.

EXAMPLE 15

Preparation of (S)-2-[1-(6-Chloroimidazo[2,1-b]thiazole-5-sulfonyl)-1H-indol-3-yl]-1-methylethylamine Hydrochloride

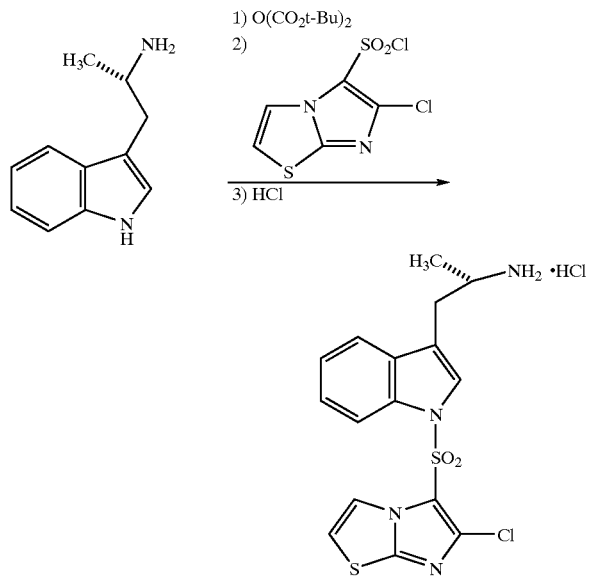

A mixture of (S)-2-(1H-Indol-3-yl)-1-methylethylamine (0.43 g, 2.5 mmol) and di-t-butyl dicarbonate (0.60 g, 2.75 mmol) in acetone is treated dropwise with aqueous K$_2$CO$_3$ (3.5 g, 25 mmol) at 0° C., allowed to warm to room temperature for 16 h, concentrated to an aqueous residue and extracted with EtOAc. The extracts are combined, dried over MgSO$_4$ and concentrated in vacuo to dryness. This residue is chromatographed (silica gel, 10%–50% EtOAc in hexanes as gradient eluent) to give the protected®-2-methyl tryptamine. A mixture of the protected tryptamine (0.17 g, 0.62 mmol) and 6-chloroimidazo[2,1-b]thiazole-5-sulfonyl chloride (0.16 g, 0.62 mmol) in THF is treated with potassium t-butoxide (77 mg, 0.68 mmol) at room temperature, stirred for 1 H, poured into saturated NaHCO$_3$ and extracted with EtOAc. The extracts are combined, dried over Na$_2$SO$_4$ and concentrated in vacuo. The resultant residue is dispersed in THF and 4N HCl in dioxane, stirred for 16 h, concentrated in vacuo and purified by HPLC[1] to afford the title product as a beige solid, 0.62 mg (35% yield), identified by NMR and mass spectral analyses.

[1] HPLC conditions: Hewlett Packard 1100 HPLC system; Waters Xterra C18, 2 mm×30 mm ID, 3 uM column; 5 uL injection; Solvent A: 0.02% TFA/water; Solvent B: 0.02% TFA/acetonitrile; Gradient: Time 0: 95% A; 0.2 min: 95% A; 3 min: 5% A; Flow rate 1.2 mL/min; Detection: 254 nm DAD.

EXAMPLE 16

Preparation of ®-2-[1-(6 Chloroimidazo[2,1-b]thiazole-5-sulfonyl)-1H-indol-3-yl]-1-methylethylamine Hydrochloride

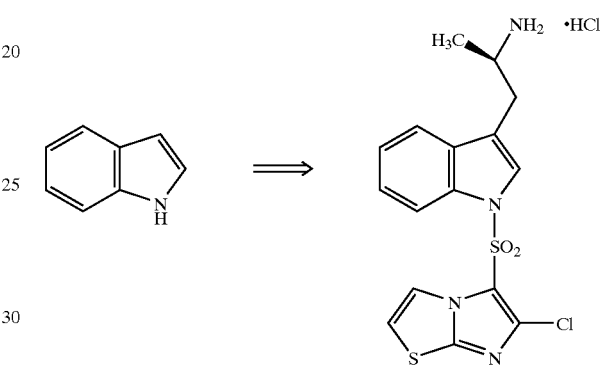

Using essentially the same procedures described hereinabove and employing F-moc-D-alanine as starting material, the title product is obtained and identified by HPLC and mass spectral analyses.

EXAMPLES 17–40

Preparation of Indolylalkylamine Derivatives

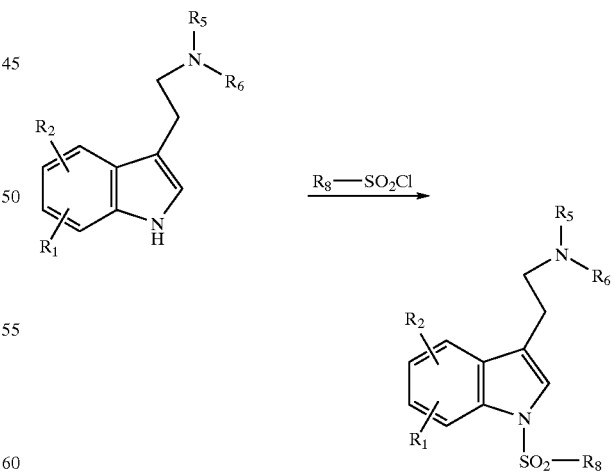

Using essentially the same procedures described hereinabove and employing the appropriate indole substrate and sulfonyl halide, the compounds shown in Table II are obtained and identified by HPLC and mass spectral analyses.

TABLE II

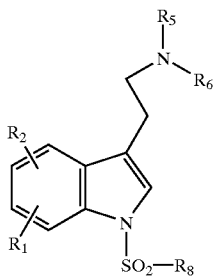

| Ex. No. | $R_1$ | $R_2$ | $R_5$ | $R_6$ | $R_4$ | HPLC[1] | M + H |
|---|---|---|---|---|---|---|---|
| 17 | H | H | H | H | 2-chloroimidazo[1,2-a]pyrid-3-yl | 1.69 | 375.8 |
| 18 | H | H | H | H | 2,6-dichloroimidazol[2,1-b]thiazol-5-yl | 1.85 | 416.3 |
| 19 | H | H | H | H | 2-chlorobenzo(d)imidazol-[2,1-b]thiazol-5-yl | 1.88 | 431.9 |
| 20 | H | H | H | $CH_3$ | 2-chloroimidazo[1,2-a]pyrid-3-yl | 1.78 | 389.9 |
| 21 | H | H | H | $CH_3$ | 2,6-dichloroimidazo[2,1-b]thiazol-5-yl | 1.84 | 430.3 |
| 22 | H | H | H | $CH_3$ | 2-chlorobenzo(d)imidazo[2,1-b]thiazol-5-yl | 1.88 | 445.9 |
| 23 | H | H | $CH_3$ | $CH_3$ | 2-chloroimidazo[1,2-a]pyrid-3-yl | 1.80 | 403.9 |
| 24 | H | H | $CH_3$ | $CH_3$ | 2,6-dichloroimidazo[2,1-b]thiazol-5-l | 1.90 | 444.4 |
| 25 | H | H | $CH_3$ | $CH_3$ | 2-chlorobenzo(d)imidazo[2,1-b]thiazol-5-yl | 1.89 | 459.9 |
| 26 | H | 5-Cl | H | H | 6-chloroimidazo[2,1-b]thiazol-5-yl | 1.87 | 416.3 |
| 27 | H | 5-Cl | H | H | 2-chloroimidazo[1,2-a]pyridy-3-yl | 1.82 | 410.3 |
| 28 | H | 5-Cl | H | H | 2,6-dichloroimidazo[2,1-b]thiazol-5-yl | 2.02 | 450.7 |
| 29 | H | 5-Cl | H | H | 2-chlorobenzo(d)imidazo[2,1-b]thiazol-5-yl | 1.98 | 466.4 |
| 30 | H | 5-$OCH_3$ | H | H | 6-chloroimidazo[2,1-b]thiazol-5-yl | 1.67 | 411.9 |
| 31 | H | 6-$OCH_3$ | H | H | 6-chloroimidazo[2,1-b]thiazol-5-yl | 1.63 | 411.9 |
| 32 | H | 5-Br | H | H | 6-chloroimidazo[2,1-b]thiazol-5-yl | 1.85 | 460.8 |
| 33 | H | 5-$OCH_2C_6H_5$ | H | H | 6-chloroimidazo[2,1-b]thiazol-5-yl | 2.00 | 488.0 |
| 34 | 5-$CH_3$ | H | H | H | 6-chloroimidazo[2,1-b]thiazol-5-yl | 1.74 | 395.9 |
| 35 | H | 6-$CH_3$ | H | H | 6-chloroimidazo[2,1-b]thiazol-5-yl | 1.73 | 395.9 |
| 36 | H | 7-$CH_3$ | H | H | 6-chloroimidazo[2,1-b]thiazol-5-yl | 2.40 | 395.9 |
| 37 | 5-OH | H | H | H | 6-chloroimidazo[2,1-b]thiazol-5-yl | 1.46 | 397.9 |
| 38 | 5-F | H | H | H | 6-chloroimidazo[2,1-b]thiazol-5-yl | 1.65 | 399.9 |
| 39 | H | 6-F | H | H | 6-chloroimidazo[2,1-b]thiazol-5-yl | 1.65 | 399.9 |
| 40 | H | H | H | H | imidazo[2,1-b]]thiazol-5-yl | 2.24 | 206 |

[1]HPLC conditions: Hewlett Packard 1100 HPLC system; Waters Xterra C18, 2 mm × 30 mm ID, 3 uM column; 5 uL injection; Solvent A: 0.02% TFA/water; Solvent B: 0.02% TFA/acetonitrile; Gradient: Time 0: 95% A; 0.2 min: 95% A; 3 min: 5% A; Flow rate 1.2 mL/min; Detection: 254 nm DAD.

EXAMPLE 41

Preparation of 3-(Fluoro-1H-indol-3-yl)propan-1-ol

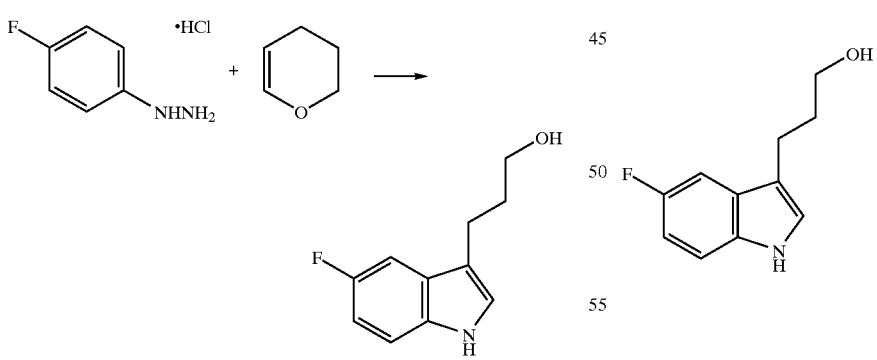

A stirred suspension of 4-fluorophenylhydrazine hydrochloride (8.13 g, 50 mmol) in a mixture of water and dioxane is treated with a solution of 3,4-dihydro-2H-pyran (4.6 ml, 50 mmol) over a period of 5 min, heated at 100° C. for 18 h, cooled, diluted with ether and filtered. The filtrate is dried over $NaSO_4$ and concentrated in vacuo. The resultant residue is purified by flash chromatography (silica gel, 1:1 EtOAc/hexane) to give the title product as an oil, 8.31 g (86% yield), identified by NMR and mass spectral analyses.

EXAMPLE 42

Preparation of 3-(3-Bromopropyl)-5-fluoro-1H-indole

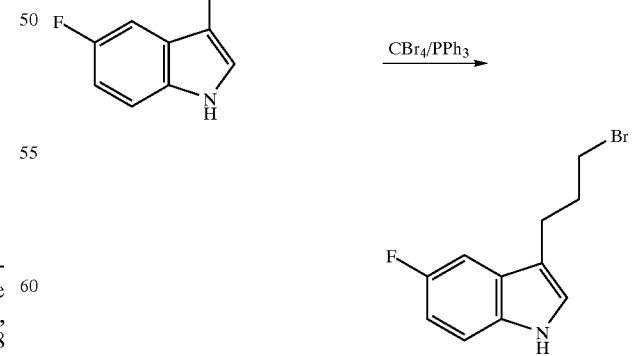

A mixture of 3-(5-fluoro-1H-indol-3-yl)-propan-1-ol (2.15 g, 11.2 mmol), carbon tetrabromide (4.80 g, 14.5 mmol) and triphenylphosphine (4.40 g, 16.7 mmol) in methylene chloride is stirred for 1 h and concentrated in vacuo. The resultant residue is purified by flash chromatography (silica gel, EtOAc/hexane 3/7) to afford the title product as an oil, 1.97 g (69% yield), identified by NMR and mass spectral analyses.

EXAMPLE 43

Preparation of 3-(3-Azidopropyl)-5-fluoro-1H-indole

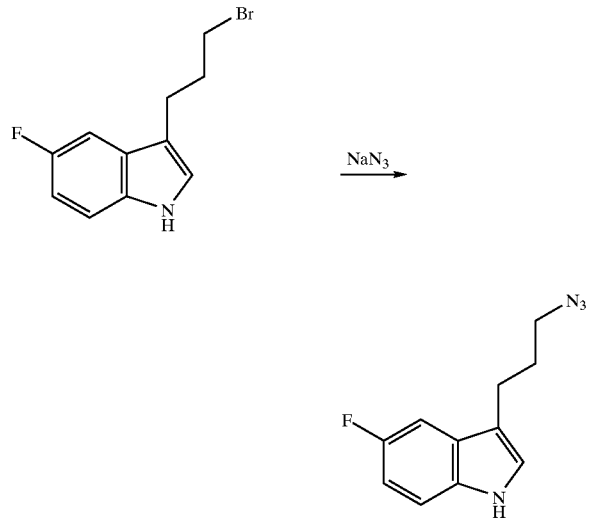

A solution of 3-(3-bromopropyl)-5-flouro-1H-indole (0.95 g, 3 mmol) and sodium azide (0.59 g, 9 mmol) in anhydrous dimethyl formamide is stirred at 60° C. for 18 h, poured into water and extracted with methylene chloride. The extracts are combined, washed with water, dried over $Na_2SO_4$ and concentrated in vacuo. The resultant residue is purified by flash chromatography (silica gel, EtOAc/hexane: 3/7) to afford the title product as a clear oil, 0.98 g (91% yield), identified by NMR and mass spectral analyses.

EXAMPLE 44

Preparation of 3-(3-Azidopropyl)-1-[(6-chloroimidazo[2,1-b][1,3]thiazol-5-yl)sulfonyl]-5-fluoro-1H-indole

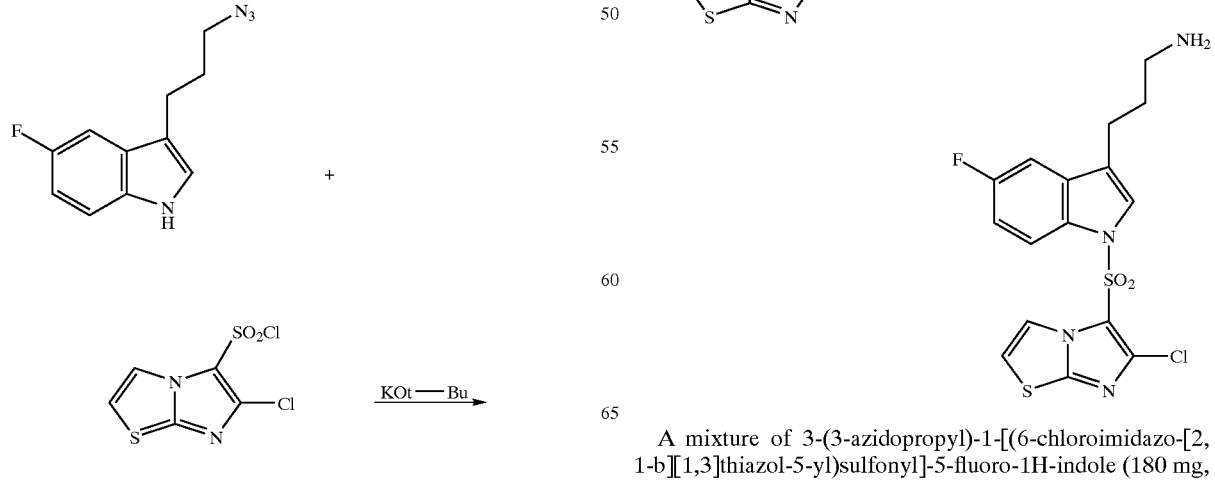

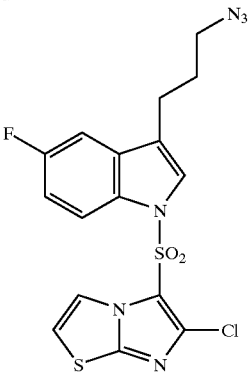

A stirred solution of 3-(3-azidopropyl)-5-fluoro-1H-indole (150 mg, 0.53 mmol) in THF is treated with KOt-Bu (0.55 ml, 0.55 mmol, 1M in THF solution) under nitrogen at room temperature, stirred for 30 min, treated with 6-chloroimidazo[2,1-b]thiazole-5-sulfonylchloride (141 mg, 0.55 mmol), stirred for 18 h at room temperature, quenched with 1N HCl and water and diluted with EtOAc. The two phases are separated and the aqueous phase is extracted with EtOAc. The extracts are combined with the organic phase and are dried over $MgSO_4$ and concentrated in vacuo. The resultant residue is purified by flash chromatography (silica gel, EtOAc/hexane: 3/7) to give the title product as a yellow solid, 203 mg (88% yield), mp 84–86° C., identified by NMR and mass spectral analyses.

EXAMPLE 45

Preparation of 3-{1-[(6-Chloroimidazo[2,1-b][1,3]thiazol-5-yl)sulfonyl]-5-fluoro-1H-indol-3-yl}propan-1-amine

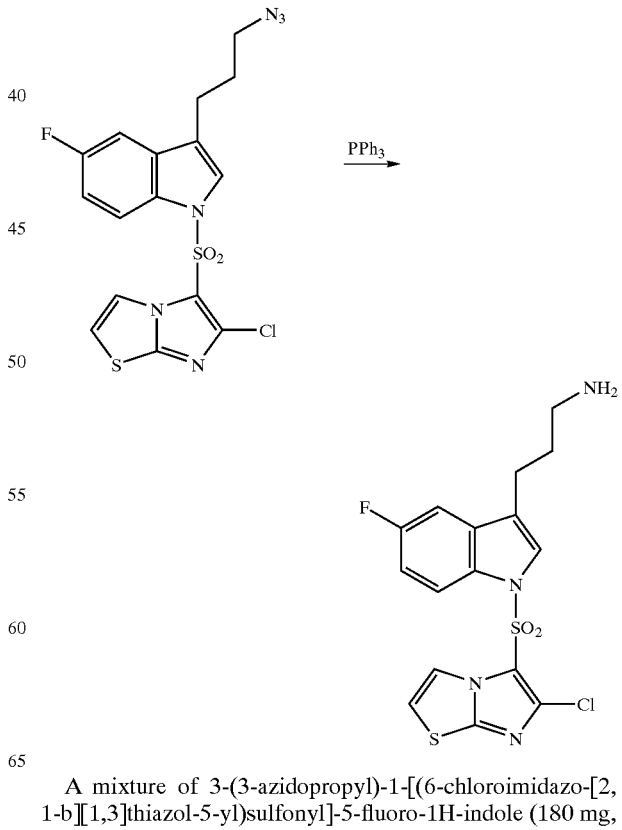

A mixture of 3-(3-azidopropyl)-1-[(6-chloroimidazo-[2,1-b][1,3]thiazol-5-yl)sulfonyl]-5-fluoro-1H-indole (180 mg, 0.41 mmol) and triphenylphosphine (161 mg, 0.62 mmol in THF and water is stirred under nitrogen for 24 h at room temperature and concentrated in vacuo. The resultant residue is purified by flash chromatography (silica gel, EtOAc/ 2M NH$_3$ in MeOH: 98/2) to afford the title product as an off-white solid, 132 mg (78% yield), mp 139–141° C., identified by NMR and mass spectral analyses.

EXAMPLE 46

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM MgCl$_2$ and 0.5 mM EDTA and 20 µl of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_I$ values of test compounds with 95% confidence limits. A linear regression line of data points is plotted, from which the IC$_{50}$ value is determined and the K$_I$ value is determined based upon the following equation:

$$K_I = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table III, below.

TABLE III

| Test Compound (Ex. No.) | 5-HT6 Binding Ki (nM) |
| --- | --- |
| 1 | 2 |
| 3 | 19 |
| 4 | 1 |
| 5 | 4 |
| 6 | 5 |
| 7 | 7 |
| 8 | 51 |
| 9 | 5 |
| 10 | 41 |
| 11 | 30 |
| 12 | 2 |
| 15 | 6 |
| 16 | 2 |
| 17 | 14 |
| 18 | 8 |
| 20 | 11 |
| 21 | 12 |
| 22 | 51 |
| 23 | 10 |
| 24 | 10 |
| 25 | 37 |
| 30 | 11 |
| 31 | 13 |
| 32 | 74 |
| 33 | 169 |
| 34 | 31 |
| 35 | 6 |
| 36 | 348 |
| 37 | 4 |
| 38 | 9 |
| 39 | 5 |
| 40 | 1.2 |
| 45 | 48 |

| Comparative Examples | 5-HT6 Binding Ki (nM) |
| --- | --- |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:
1. A compound of formula I

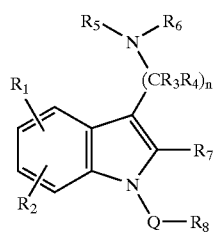

(I)

wherein
Q is $SO_2$, CO, $CONR_9$ or $CSNR_{10}$;
n is an integer of 2 or 3;
$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;
$R_7$ is H, halogen, or a $C_1$–$C_6$alkyl, $C_1$–$C_6$alkoxy, aryl or heteroaryl group each optionally substituted;
$R_8$ is an optionally substituted 8- to 13-membered bicyclic or tricyclic ring system having a N atom at the bridgehead and optionally containing 1, 2 or 3 additional heteroatoms selected from N, O or S;
m is 0 or an integer of 1 or 2;
$R_9$ and $R_{10}$ are each independently H or a $C_1$–$C_6$alkyl, aryl or heteroaryl group each optionally substituted;
$R_{12}$, $R_{13}$, $R_{19}$ and $R_{23}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_{14}$, $R_{15}$ and $R_{22}$ are each independently H or an optionally substituted $C_1$–$C_6$alkyl group; and
$R_{16}$, $R_{17}$, $R_{18}$, $R_{20}$ and $R_{21}$ are each independently H or an optionally substituted $C_1$–$C_4$alkyl group; or $R_{20}$ and $R_{21}$ may be taken together with the atom to which they are attached to form a 5- to 7-membered ring optionally containing another heteroatom selected from O, N or S; or
the stereoisomers thereof or the pharmaceutically acceptable salts thereof.
2. The compound according to claim 1 wherein Q is $SO_2$.
3. The compound according to claim 1 wherein n is 2.
4. The compound according to claim 1 wherein $R_8$ is an optionally substituted imidazo[2,1-b][1,3]thiazolyl ring system.
5. The compound according to claim 2 wherein $R_7$ is H.
6. The compound according to claim 5 wherein n is 2.
7. The compound according to claim 6 wherein $R_3$ and $R_4$ are H.
8. The compound according to claim 7 wherein $R_8$ is 6-chloro-imidazo[2,1-b][1,3]thiazol-5-yl.
9. The compound according to claim 7 selected from the group consisting of:
2-{1-[(6-chloroimidazo[2,1-b][1,3]thiazol-5-yl) sulfonyl]-1H-indol-3-yl}ethylamine;
2-{1-[(imidazo[2,1-b][1,3]thiazol-5-yl)sulfonyl]-1H-indol-3-yl}ethylamine;
{2-[1-(6-chloro-imidazo[2,1-b][1,3]thiazole-5-sulfonyl)-1H-indol-3-yl]ethyl}methylamine;
{2-[1-(6-chloro-imidazo[2,1-b][1,3]thiazole-5-sulfonyl)-1H-indol-3-yl]ethyl}dimethylamine;
benzyl-{2-[1-(6-chloro-imidazo[2,1-b][1,3]thiazole-5-sulfonyl)-1H-indol-3-yl]ethyl}amine;
1-(6-chloro-imidazo[2,1-b][1,3]thiazole-5-sulfonyl)-3-(2-pyrrolidin-1-ylethyl)-1H-indole;
1-(6-chloro-imidazo[2,1-b][1,3]thiazole-5-sulfonyl)-3-[2-(4-methylpiperazin-1-yl)ethyl]-1H-indole;
1-(6-chloro-imidazo[2,1-b][1,3]thiazole-5-sulfonyl)-3-(2-piperidin-1-ylethyl)-1H-indole;
benzyl-{2-[1-(6-chloro-imidazo[2,1-b][1,3]thiazole-5-sulfonyl)-1H-indol-3-yl]ethyl}methylamine;
{2-[1-(6-chloro-imidazo[2,1-b][1,3]thiazole-5-sulfonyl)-1H-indol-3-yl]ethyl}phenethylamine;
1-{2-[1-(6-chloro-imidazo[2,1-b][1,3]thiazole-5-sulfonyl)-1H-indol-3-yl]ethyl}pyrrolidine-2-carboxylic acid;
2-[1-(6-chloro-imidazo[2,1-b][1,3]thiazole-5-sulfonyl)-1H-indol-3-yl]-1-methylethylamine;
(R)-2-[1-(6-chloro-imidazo[2,1-b][1,3]thiazole-5-sulfonyl)-1H-indol-3-yl]-1-methylethylamine;
(S)-2-[1-(6-chloro-imidazo[2,1-b][1,3]thiazole-5-sulfonyl)-1H-indol-3-yl]-1-methylethylamine;
2-[1-(2-chloro-imidazo[1,2-a]pyridine-3-sulfonyl)-1H-indol-3-yl]ethylamine;
2-[1-(2,6-dichloro-imidazo[2,1-b][1,3]thiazole-5-sulfonyl)-1H-indol-3-yl]ethylamine;
2-[1-(2-chloro-benzo[d]imidazo[2,1-b][1,3]thiazole3-sulfonyl)-1H-indol-3-yl]ethylamine;
{2-[1-(2-chloro-imidazo[1,2-a]pyridine-3-sulfonyl)-1H-indol-3-yl]ethyl}methylamine;
{2-[1-(2,6-dichloro-imidazo[2,1-b][1,3]thiazole-5-sulfonyl)-1H-indol-3-yl]ethyl}methylamine;
{2-[1-(2-chloro-benzo[d]imidazo[2,1-b][1,3]thiazole-3-sulfonyl)-1H-indol-3-yl]ethyl}methylamine;
{2-[1-(2-chloro-imidazo[1,2-a]pyridine-3-sulfonyl)-1H-indol-3-yl]ethyl}dimethyamine;
{2-[1-(2,6-dichloro-imidazo[2,1-b][1,3]thiazole-5-sulfonyl)-1H-indol-3-yl]ethyl}dimethylamine;
{2-[1-(2-chloro-benzo[d]imidazo[2,1-b][1,3]thiazole-3-sulfonyl)-1H-indol-3-yl]ethyl}dimethylamine;
2-[5-chloro-1-(6-chloro-imidazo[2,1-b][1,3]thiazole-5-sulfonyl)-1H-indol-3-yl]ethylamine;
2-[5-chloro-1-(2-chloro-imidazo[1,2-a]pyridine-3-sulfonyl)-1H-indol-3-yl]ethylamine;
2-[5-chloro-1-(2,6-dichloro-imidazo[2,1-b][1,3]thiazole-5-sulfonyl)-1H-indol-3-yl]ethylamine;
2-[5-chloro-1-(2-chloro-benzo[d]imidazo[2,1-b][1,3]thiazole-3-sulfonyl)-1H-indol-3-yl]-ethylamine;
2-[1-(6-chloro-imidazo[2,1-b][1,3]thiazole-5-sulfonyl)-5-methoxy-1H-indol-3-yl]ethylamine;
2-[1-(6-chloro-imidazo[2,1-b][1,3]thiazole-5-sulfonyl)-6-methoxy-1H-indol-3-yl]ethylamine;

2-[5-bromo-1-(6-chloro-imidazo[2,1-b][1,3]thiazole-5-sulfonyl)-1H-indol-3-yl]ethylamine;

2-[5-benzyloxy-1-(6-chloro-imidazo[2,1-b][1,3]thiazole-5-sulfonyl)-1H-indol-3-yl]ethylamine;

2-[1-(6-chloro-imidazo[2,1-b][1,3]thiazole-5-sulfonyl)-5-methyl-1H-indol-3-yl]ethylamine;

2-[1-(6-chloro-imidazo[2,1-b][1,3]thiazole-5-sulfonyl)-6-methyl-1H-indol-3-yl]ethylamine;

2-[1-(6-chloro-imidazo[2,1-b][1,3]thiazole-5-sulfonyl)-7-methyl-1H-indol-3-yl]ethylamine;

3-(2-amino-ethyl)-1-(6-chloro-imidazo[2,1-b][1,3]thiazole-5-sulfonyl)-1H-indol-5-ol;

2-[1-(6-chloro-imidazo[2,1-b][1,3]thiazole-5-sulfonyl)-5-fluoro-1H-indol-3-yl]ethylamine;

2-[1-(6-chloro-imidazo[2,1-b][1,3]thiazole-5-sulfonyl)-6-fluoro-1H-indol-3-yl]ethylamine;

the stereoisomers thereof; and
the pharmaceutically acceptable salts thereof.

10. A method for the treatment of a disorder of the central nervous system related to or affected by the 5-HT6 receptor selected from the group consisting of: an anxiety disorder; and a cognitive disorder in a patient in need thereof which comprises providing to said patient a therapeutically effective amount of a compound of formula I

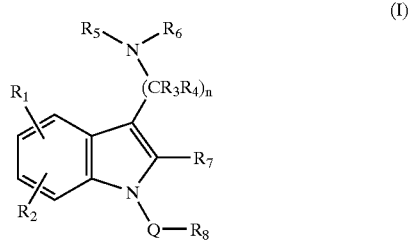

wherein
Q is $SO_2$, CO, $CONR_9$ or $CSNR_{10}$;
n is an integer of 2 or 3;
$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;
$R_7$ is H, halogen, or a $C_1$–$C_6$alkyl, $C_1$–$C_6$alkoxy, aryl or heteroaryl group each optionally substituted;
$R_8$ is an optionally substituted 8- to 13-membered bicyclic or tricyclic ring system having a N atom at the bridgehead and optionally containing 1, 2 or 3 additional heteroatoms selected from N, O or S;
m is 0 or an integer of 1 or 2;
$R_9$ and $R_{10}$ are each independently H or a $C_1$–$C_6$alkyl, aryl or heteroaryl group each optionally substituted;

$R_{12}$, $R_{13}$, $R_{19}$ and $R_{23}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$, $R_{15}$ and $R_{22}$ are each independently H or an optionally substituted $C_1$–$C_6$alkyl group; and $R_{16}$, $R_{17}$, $R_{18}$, $R_{20}$ and $R_{21}$ are each independently H or an optionally substituted $C_1$–$C_4$alkyl group; or $R_{20}$ and $R_{21}$ may be taken together with the atom to which they are attached to form a 5- to 7-membered ring optionally containing another heteroatom selected from O, N or S;
or
the stereoisomers thereof or the pharmaceutically acceptable salts thereof.

11. The method according to claim 10 wherein said disorder is schizophrenia or depression.

12. The method according to claim 10 wherein said disorder is Alzheimer's disease or Parkinson's disease.

13. The method according to claim 10 wherein said disorder is attention deficit disorder or obsessive compulsive disorder.

14. A pharmaceutical composition which comprises a pharmaceutically acceptable carrier and an effective amount of a compound of formula I

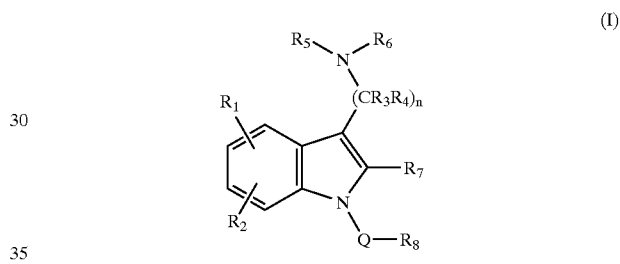

wherein
Q is $SO_2$, CO, $CONR_9$ or $CSNR_{10}$;
n is an integer of 2 or 3;
$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_3$ and $R_4$ are each independently H or an optionally substituted $C_1$–$C_6$alkyl group;
$R_5$ and $R_6$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;
$R_7$ is H, halogen, or a $C_1$–$C_6$alkyl, $C_1$–$C_6$alkoxy, aryl or heteroaryl group each optionally substituted;
$R_8$ is an optionally substituted 8- to 13-membered bicyclic or tricyclic ring system having a N atom at the bridgehead and optionally containing 1, 2 or 3 additional heteroatoms selected from N, O or S;
m is 0 or an integer of 1 or 2;
$R_9$ and $R_{10}$ are each independently H or a $C_1$–$C_6$alkyl, aryl or heteroaryl group each optionally substituted;
$R_{12}$, $R_{13}$, $R_{19}$ and $R_{23}$ are each independently H or a $C_1$–$C_6$alkyl, $C_2$–$C_6$alkenyl, $C_2$–$C_6$alkynyl, $C_3-C_6$cycloalkyl, cycloheteroalkyl, aryl or heteroaryl group each optionally substituted;

$R_{14}$, $R_{15}$ and $R_{22}$ are each independently H or an optionally substituted $C_1-C_6$alkyl group; and $R_{16}$, $R_{17}$, $R_{18}$, $R_{20}$ and $R_{21}$ are each independently H or an optionally substituted $C_1-C_4$alkyl group; or $R_{20}$ and $R_{21}$ may be taken together with the atom to which they are attached to form a 5- to 7-membered ring optionally containing another heteroatom selected from O, N or S; or the stereoisomers thereof or the pharmaceutically acceptable salts thereof.

15. The composition according to claim 14 having a formula I compound wherein Q is $SO_2$.

16. The composition according to claim 15 having a formula I compound wherein n is 2 and $R_7$ is H.

17. The composition according to claim 16 having a formula I compound wherein $R_3$ and $R_4$ are H and $R_8$ is 6-chloroimidazo[2,1-b][1,3]thiazol-5-yl.

18. The composition according to claim 16 having a formula I compound selected from the group consisting of:

2-{1-[(6-chloroimidazo[2,1-b][1,3]thiazol-5yl)sulfonyl]-1H-indol-3-yl}ethylamine;

2-{1-[(imidazo[2,1-b][1,3]thiazol-5-yl)sulfonyl]-1H-indol-3-yl}ethylamine;

{2-[1-(6-chloro-imidazo[2,1-b][1,3]thiazole-5-sulfonyl)-1H-indol-3-yl]ethyl}methylamine;

{2-[1-(6-chloro-imidazo[2,1-b][1,3]thiazole-5-sulfonyl)-1H-indol-3-yl]ethyl}dimethylamine;

benzyl-{2-[1-(6-chloro-imidazo[2,1-b][1,3]thiazole-5-sulfonyl)-1H-indol-3-yl]ethyl}amine;

1-(6-chloro-imidazo[2,1-b][1,3]thiazole-5-sulfonyl)-3-(2-pyrrolidin-1-ylethyl)-1H-indole;

1-(6-chloro-imidazo[2,1-b][1,3]thiazole-5-sulfonyl)-3-[2-(4-methylpiperazin-1-yl)ethyl]-1H-indole;

1-(6-chloro-imidazo[2,1-b][1,3]thiazole-5-sulfonyl)-3-(2-piperidin-1-ylethyl)-1H-indole;

benzyl-{2-[1-(6-chloro-imidazo[2,1-b][1,3]thiazole-5-sulfonyl)-1H-indol-3-yl]ethyl}methylamine;

{2-[1-(6-chloro-imidazo[2,1-b][1,3]thiazole-5-sulfonyl)-1H-indol-3-yl]ethyl}phenethylamine;

1-{2-[1-(6-chloro-imidazo[2,1-b][1,3]thiazole-5-sulfonyl)-1H-indol-3-yl]ethyl}pyrrolidine-2-carboxylic acid;

2-[1-(6-chloro-imidazo[2,1-b][1,3]thiazole-5-sulfonyl)-1H-indol-3-yl]-1-methylethylamine;

(R)-2-[1-(6-chloro-imidazo[2,1-b][1,3]thiazole-5-sulfonyl)-1H-indol-3-yl]-1-methylethylamine;

(S)-2-[1-(6-chloro-imidazo[2,1-b][1,3]thiazole-5-sulfonyl)-1H-indol-3-yl]-1-methylethylamine;

2-[1-(2-chloro-imidazo[1,2-a]pyridine-3-sulfonyl)-1H-indol-3-yl]ethylamine;

2-[1-(2,6-dichloro-imidazo[2,1-b][1,3]thiazole-5-sulfonyl)-1H-indol-3-yl]ethylamine;

2-[1-(2-chloro-benzo[d]imidazo[2,1-b][1,3]thiazole-3-sulfonyl)-1H-indol-3-yl]ethylamine;

{2-[1-(2-chloro-imidazo[1,2-a]pyridine-3-sulfonyl)-1H-indol-3-yl]ethyl}methylamine;

{2-[1-(2,6-dichloro-imidazo[2,1-b][1,3]thiazole-5-sulfonyl)-1H-indol-3-yl]ethyl}methylamine;

{2-[1-(2-chloro-benzo[d]imidazo[2,1-b][1,3]thiazole-3-sulfonyl)-1H-indol-3-yl]ethyl}methylamine;

{2-[1-(2-chloro-imidazo[1,2-a]pyridine-3-sulfonyl)-1H-indol-3-yl]ethyl}dimethyamine;

{2-[1-(2,6-dichloro-imidazo[2,1-b][1,3]thiazole-5-sulfonyl)-1H-indol-3-yl]ethyl}dimethylamine;

{2-[1-(2-chloro-benzo[d]imidazo[2,1-b][1,3]thiazole-3-sulfonyl)-1H-indol-3-yl]ethyl}dimethylamine;

2-[5-chloro-1-(6-chloro-imidazo[2,1-b][1,3]thiazole-5-sulfonyl)-1H-indol-3-yl]ethylamine;

2-[5-chloro-1-(2-chloro-imidazo[1,2-a]pyridine-3-sulfonyl)-1H-indol-3-yl]ethylamine;

2-[5-chloro-1-(2,6-dichloro-imidazo[2,1-b][1,3]thiazole-5-sulfonyl)-1H-indol-3-yl]ethylamine;

2-[5-chloro-1-(2-chloro-benzo[d]imidazo[2,1-b][1,3]thiazole-3-sulfonyl)-1H-indol-3-yl]-ethylamine;

2-[1-(6-chloro-imidazo[2,1-b][1,3]thiazole-5-sulfonyl)-5-methoxy-1H-indol-3-yl]ethylamine;

2-[1-(6-chloro-imidazo[2,1-b][1,3]thiazole-5-sulfonyl)-6-methoxy-1H-indol-3-yl]ethylamine;

2-[5-bromo-1-(6-chloro-imidazo[2,1-b][1,3]thiazole-5-sulfonyl)-1H-indol-3-yl]ethylamine;

2-[5-benzyloxy-1-(6-chloro-imidazo[2,1-b][3]thiazole-5-sulfonyl)-1H-indol-3-yl]ethylamine;

2-[1-(6-chloro-imidazo[2,1-b][1,3]thiazole-5-sulfonyl)-5-methyl-1H-indol-3-yl]ethylamine;

2-[1-(6-chloro-imidazo[2,1-b][1,3]thiazole-5-sulfonyl)-6-methyl-1H-indol-3-yl]ethylamine;

2-[1-(6-chloro-imidazo[2,1-b][1,3]thiazole-5-sulfonyl)-7-methyl-1H-indol-3-yl]ethylamine;

3-(2-amino-ethyl)-1-(6-chloro-imidazo[2,1-b][1,3]thiazole-5-sulfonyl)-1H-indol-5-ol;

2-[1-(6-chloro-imidazo[2,1-b][1,3]thiazole-5-sulfonyl)-5-fluoro-1H-idol-3-yl]ethylamine;

2-[1-(6-chloro-imidazo[2,1-b][1,3]thiazole-5-sulfonyl)-6-fluoro-1H-indol-3-yl]ethylamine;

the stereoisomers thereof; and the pharmaceutically acceptable salts thereof.

19. A process for the preparation of a compound of formula Id

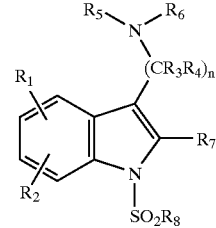

(Id)

wherein n is an integer of 2 or 3;

$R_1$ and $R_2$ are each independently H, halogen, CN, $OCO_2R_{12}$, $CO_2R_{13}$, $CONR_{14}R_{15}$, $CNR_{16}NR_{17}R_{18}$, $SO_mR_{19}$, $NR_{20}R_{21}$, $OR_{22}$, $COR_{23}$ or a $C_1-C_6$alkyl, $C_2-C_6$alkenyl, $C_2-C_6$alkynyl, $C_3-C_6$cycloalkyl, cycloheteroalkyl, aryl or heteroaryl group each optionally substituted;

$R_3$ and $R_4$ are each independently H or an optionally substituted $C_1-C_6$alkyl group;

$R_5$ and $R_6$ are each independently a $C_1-C_6$alkyl, $C_2-C_6$alkenyl, $C_2-C_6$alkynyl, $C_3-C_6$cycloalkyl, cycloheteroalkyl, aryl or heteroaryl group each optionally substituted, or $R_5$ and $R_6$ may be taken together with the atom to which they are attached to form an optionally substituted 5- to 7-membered ring optionally containing an additional heteroatom selected from O, N or S;

$R_7$ is H, halogen, or a $C_1$–$C_6$alkyl, $C_1$–$C_6$alkoxy, aryl or heteroaryl group each optionally substituted;

$R_8$ is an optionally substituted 8- to 13-membered bicyclic or tricyclic ring system having a N atom at the bridgehead and optionally containing 1, 2 or 3 additional heteroatoms selected from N, O or S;

m is 0 or an integer of 1 or 2;

$R_9$ and $R_{10}$ are each independently H or a $C_1$–$C_6$alkyl, aryl or heteroaryl group each optionally substituted;

$R_{12}$, $R_{13}$ and $R_{19}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{14}$, $R_{15}$ and $R_{22}$ are each independently H or an optionally substituted $C_1$–$C_6$alkyl group; and $R_{16}$, $R_{17}$, $R_{18}$, $R_{20}$ and $R_{21}$ are each independently H or an optionally substituted $C_1$–$C_4$alkyl group; or $R_{20}$ and $R_{21}$ may be taken together with the atom to which they are attached to form a 5- to 7-membered ring optionally containing another heteroatom selected from O, N or S which process comprises reacting a compound of formula XVIII

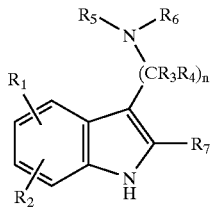

(XVIII)

wherein n, $R_1$, $R_2$, $R_3$, $R_4$, $R_5$, $R_6$ and $R_7$ are as defined hereinabove for formula Id with a sulfonyl chloride $R_8SO_2Cl$, in the presence of a base optionally in the presence of a solvent.

* * * * *